United States Patent [19]

Blount, Jr. et al.

[11] Patent Number: 5,025,086
[45] Date of Patent: Jun. 18, 1991

[54] NOVEL TRIFUNCTIONAL MONOMER COMPOUNDS, POLYESTERS DERIVED THEREFROM AND THERMOSETTING COATING COMPOSITIONS CONTAINING THE POLYESTERS

[75] Inventors: William W. Blount, Jr.; Joseph R. Zoeller, both of Kingsport, Tenn.

[73] Assignee: Eastman Kodak Company, Rochester, N.Y.

[21] Appl. No.: 612,154

[22] Filed: Nov. 13, 1990

[51] Int. Cl.$^5$ .............................................. C08G 63/02
[52] U.S. Cl. .................................. 528/272; 528/274; 528/295.5; 528/296; 528/297; 528/298; 528/300; 528/304; 528/306; 528/307; 528/308; 528/308.6; 525/450; 524/700; 524/745; 428/480; 560/64; 568/665
[58] Field of Search ...................... 528/272, 274, 295.5, 528/296, 297, 298, 300, 304, 306, 307, 308, 308.6; 525/450; 524/745, 700; 428/480; 560/64; 568/665

[56] References Cited

U.S. PATENT DOCUMENTS 4,965,399 10/1990 Zoeller et al. ........................ 560/64

OTHER PUBLICATIONS

Conrad et al., Org. Syn., Coll, vol. II, 167 (1943).
Rylander, Hydrogenation Methods, in the Best Synthetic Methods Series, Academic Press, N.Y. (1985).

Primary Examiner—John Kight, III
Assistant Examiner—Sam A. Acquah
Attorney, Agent, or Firm—Bernard J. Graves, Jr.; William P. Heath, Jr.

[57] ABSTRACT

Provided are 1,5-bis(4-carboxycyclohexyl)-3-pentanol and its esters and processes for their preparation. Also provided are polyester compositions containing this residue, thermosetting coating compositions containing the polyesters, and coatings and casted or molded articles made therefrom.

5 Claims, No Drawings

TRIFUNCTIONAL MONOMER COMPOUNDS, POLYESTERS DERIVED THEREFROM AND THERMOSETTING COATING COMPOSITIONS CONTAINING THE POLYESTERS

FIELD OF THE INVENTION

This invention relates to 1,5-bis(4-carboxycyclo-hexyl)-3-pentanol and esters thereof and to processes for the preparation of such compounds and esters. This invention further pertains to polyesters derived from such compounds and esters and to coating compositions containing the polyesters.

BACKGROUND OF THE INVENTION

It is known that benzaldehyde and certain substituted benzaldehydes may be condensed with acetone to obtain certain unsubstituted and substituted 1,5-diaryl-penta-1,4-dien-3-one compounds, also referred to as dibenzalacetones. Typical procedures are described in Org. Syn., Coll. Vol. II, 167 (1943) and British Patent 1,442,133. The preparation of certain unsubstituted and substituted 1,5-diaryl-3-pentanols by the catalytic hydrogenation of the 1,5-diaryl-penta-1,4-dien-3-one compounds also is described in the literature. British Patent 1,442,133 discloses the hydrogenation of 1,5-bis(3',5'-di-t-butyl-4,-hydroxyphenyl)penta-1,4-dien-3-one to the corresponding 1,5-bis(3',5'-di-t-butyl-4,.hydroxyphenyl)pentanol over 5% palladium on carbon at a pressure of 420 to 580 psig pressure Ipat'ev and Orlov, [Compt. Rend., 184, 751 (C.A. 21:1974; 1927), Bull. Soc. Chim., 41, 862 (C.A. 21:3042; 1927), J. Russ. Phys.-Chem. Soc., 59, 537 (C.A. 22:1151; 1927)]describe the catalytic hydrogenation of 1,5-diphenylpenta-1,4-dien-3-one using nickel catalyst and mention specifically that nickel oxide, at 170°–180° C. and 980–1400 psi hydrogen pressure, gives the ketone, 1,5-diphenyl-3.pentanone. They also state that copper oxide is not an effective catalyst. The hydrogenation of 1,5.diphenyl-penta-1,4-dien-3-one to 1,5-diphenyl-3-pentanol at lower pressure and Raney nickel is disclosed in Compt. Rend., 229, 460, (1949). A similar catalytic hydrogenation using a "skeletal" nickel catalyst at 2100 psi hydrogen pressure is disclosed in J. Organomet. Chem., 153, 181 (1978). According to Chem. Ber., 74B, 1195 (1941), a platinum oxide catalyst gives a 1:1 mixture of 1,5-diphenyl-3-pentanone and 1,5-diphenyl3-pentanol.

SUMMARY OF THE INVENTION

This invention provides novel monomers, 1,5-bis(4-carboxycyclohexyl)-3-pentanol and esters thereof and processes for their preparation. Also provided are curable polyester compositions and cross-linkable enamel compositions comprising said novel monomers. Thermosetting coatings resulting therefrom have been found to possess an outstanding balance of hardness and flexibility. This invention also provides casted or molded articles and coatings comprised of the novel polyesters.

DETAILED DESCRIPTION OF THE INVENTION

The present invention provides a compound of Formula (1):

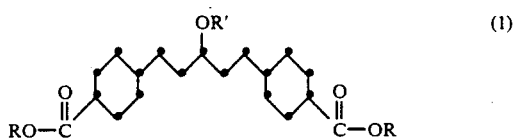

wherein R is hydrogen or $C_1$–$C_6$ alkyl, and R' is hydrogen or $C_1$–$C_6$ alkanoyl.

In a preferred aspect of the present invention, R is $C_1$–$C_6$, most preferably methyl.

Compounds of Formula (1) may be prepared as shown below in Scheme (1):

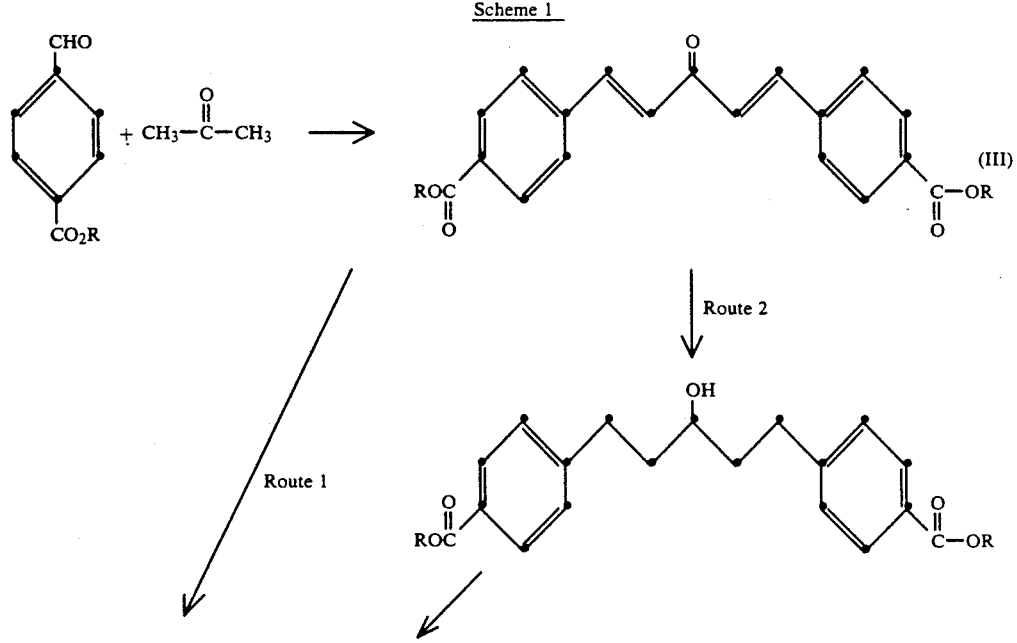

-continued

Scheme 1

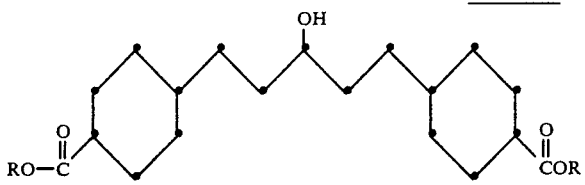

The first step of the above-described process is carried out by reacting approximately 2 moles of the aldehyde per mole of ketone in the presence of an acidic or basic catalyst. Examples of materials which may be used as the catalyst include the alkali metal hydroxides, alkoxides and carbonates; the alkaline earth hydroxides and oxides; quaternary ammonium hydroxides such as tetra-unsubstituted or substituted alkylammonium hydroxides wherein the four alkyl residues contain a total of up to about 20 carbon atoms; alkyl- and aryl-sulfonic acids; acidic ion exchange resins such as Amberlyst 15; and mineral acids such as sulfuric and hydrochloric acid. The condensation reaction normally is conducted in the presence of an inert solvent such as aliphatic and aromatic hydrocarbons, e.g., having from about 6 to 12 carbon atoms and alkanols, e.g., having up to about 6 carbon atoms. The temperature of the condensation step can be varied substantially depending on a number of factors such as the catalyst being used, catalyst concentration, etc. Although temperatures as low as $-25°$ C. and as high as 300° C. may be used under some circumstances, the condensation reaction normally will be performed at a temperature in the range of about 0° to 140° C. Pressure is not normally important and, while pressure moderately above or below atmospheric may be used, the first step most conveniently is done at ambient pressure.

The hydrogenation may be performed in a single step by hydrogenating intermediate (III) in the presence of a supported Group VIII metal catalyst such as ruthenium, rhodium, palladium and platinum deposited on or supported by a catalyst support material such as silica, alumina, carbon, titania, etc. The preferred hydrogenation catalysts for the single step hydrogenation procedure in terms of both selectivity and yield are platinum or rhodium on carbon. The concentration of the Group VIII metal catalyst can vary substantially depending on a number of factors such as the activity and/or selectivity of the particular catalyst, the surface area of the catalyst, the hydrogenation conditions, the mode of operation, etc. For example, when using a tricklebed hydrogenation system wherein a solution of a 1,5-bis(4-alkoxycarbonylphenyl)penta-1,4-dien-3-one flows over and through one or more fixed beds of the catalyst in granular form in a hydrogen atmosphere at elevated temperature and pressure, the concentration of the catalyst relative to the reactant cannot be determined with any degree of accuracy.

The hydrogenation conditions of temperature and pressure may vary over a wide range depending, for example, on the factors referred to above concerning catalyst concentration. Furthermore, to some extent, temperature and pressure are interdependent and, thus, increasing one may permit lowering of the other. Generally, preferable hydrogenation conditions will be within the ranges of about 20° to 300° C. and about 50 to 3000 psig hydrogen. The more preferred ranges are about 150° to 250° C. and about 500 to 1500 psig hydrogen. Typically, the hydrogenation is carried out in the presence of an inert organic solvent for the intermediate 1,5-bis(4-alkoxycarbonylphenyl)penta-1,4-dien3-one. Examples of solvents which may be used include hydrocarbons such as aliphatic, cycloaliphatic and aromatic hydrocarbons containing about 6 to 12 carbon atoms, e.g., benzene, toluene, xylene, cumene, psuedocumene, diisopropylbenzene, cyclohexane, hexane, heptane, etc.; carboxylic acid esters such as alkyl carboxylates containing up to about 6 carbon atoms, e.g., methyl acetate, ethyl acetate, methyl butyrate, etc; alkanols containing up to about 6 carbon atoms, e.g., methanol, ethanol, 2-propanol, etc. The concentration of the pentadienone reactant in the solvent is not critical and is limited only by the solubility of the particular reactant in the solvent being used and economic considerations. For most reactants the preferred inert organic solvents are toluene, xylene and cyclohexane.

The product obtained from the single step hydrogenation procedure typically contains as co-product, e.g., from about 1 to 10 weight percent, the corresponding ketone, i.e., 1,5-bis(4-alkoxycarbonylcyclohexyl)-3-pentanone. Other detectable coproducts include the diester 1,5-bis(4-alkoxycarbonylcyclohexyl)pentane and compounds containing incompletely reduced rings. Since the coproducts are difunctional, their presence may not be objectionable for use of the hydrogenation product in the synthesis of polyesters, especially for hydrogenation products containing at least 95 area percent (by gas chromatography analysis) combined 1,5-bis(4-alkoxycarbonylcyclohexyl)-3-pentanol and 1,5-bis(4-alkoxycarbonylcyclohexyl)-3-pentanone. If a highly pure product is desired, the above-described rhodium- or platinum-catalyzed hydrogenation may be followed by a further reduction with a hydride reducing agent.

A second hydrogenation process as provided by the present invention comprises a two stage procedure wherein the intermediate 1,5-bis(4-alkoxycarbonylphenyl)penta-1,4-dien-3-one is hydrogenated in the presence of a copper chromite catalyst and an inert solvent to produce a 1,5-bis(4-alkoxycarbonylphenyl)-3-pentanol which then is hydrogenated in the presence of a supported Group VIII metal catalyst, e.g., those catalysts described hereinabove. The catalyst used in the hydrogenation of the 1,5-bis(4-akloxycarbonylphenyl)-3-pentanol compounds is a supported palladium catalyst, e.g., 0.1 to 1.0 weight percent palladium on alumina. The hydrogenation conditions of pressure and temperature and the inert solvents which may be used in the second, two stage, hydrogenation procedure are set forth above.

Although the single-step hydrogenation procedure is the most economical and therefore is preferred if low levels of co-products are tolerable, the second, two stage procedure may be used to produce high purity 1,5-bis(4-alkoxycarbonylcyclohexyl)-3-pentanol compounds. The corresponding bis-carboxylic acids, i.e.

compounds of Formula (I) wherein R is hydrogen, may be prepared by the hydrolysis of the diester compounds, preferably under basic conditions. Similarly, when the desired R' group is $C_1-C_6$ alkanoyl, esterification may be carried out using standard methodology.

Thus, as a further aspect of this invention, there is provided a process for preparing a compound of Formula (1):

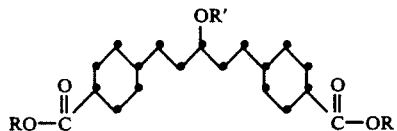

wherein R is $C_1-C_6$ alkyl and R' is hydrogen, which comprises the steps (a) reacting a compound of the formula

with acetone, wherein R is as defined above; followed by (b) catalytic hydrogenation.

As a further aspect of the present invention, there is provided a process for preparing a compound of Formula (1)

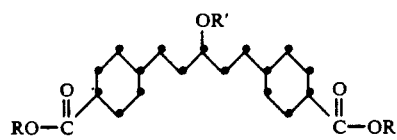

wherein R is $C_1-C_6$ alkyl and R' is hydrogen, which comprises the steps (a) reacting a compound of the formula

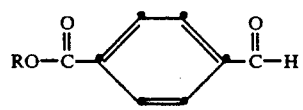

with acetone, wherein R is as defined above; followed by (b) catalytic hydrogenation using copper-chromite as catalyst to provide a compound of the formula

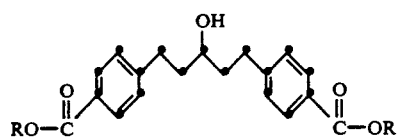

wherein R is as defined above; followed by (c) catalytic hydrogenation.

As a further aspect of the present invention, there is provided the above two aspects of the invention further comprising the treatment of the reaction product with a hydride reducing agent. This additional step may be carried out in order to achieve higher levels of the hydroxy compound, i.e., more complete reduction of the corresponding ketone. Preferably, the hydride reducing agent is selected from $NaBH_4$, KH, $NaCNBH_4$, $(CH_3CH_2CH_2CH_2)_4NBH_4$, $LiBH_4$, $(CH_3)_4NBH_4$, $(CH_3CH_2)_4NBH_4$, $BH_3$, $NaAlH_2(OCH_2CH_2OCH_3)_2$, $LiAlH(O(CH_3)_3)_3$, $LiAlH(OCH_2CH_3)_3$, $[(CH_3)_2CHCH(CH_3)_2]_2BH$, and $[(CH_3)_2CHCH_2]AlH$.

Due to the presence of two functional groups on the two cyclohexyl groups, the compounds of formula (I) exist as a mixture of three chromatographically-distinguishable entities as a result of the three possible combinations of cis and trans cyclohexyl moieties.

The incorporation of polyester intermediates having a number of reactive sites (referred to as functionality) greater than two required to manufacture branched and/or cross-linkable coatings is well known to the art. Hydroxyl-containing (e.g., 1,1,1-trimethylolpropane), carboxyl-containing (e.g., trimellitic anhydride), and mixed functional (e.g., 2,2-dimethylolpropionic acid) have all been used to prepare coatings resins and formulated thermosetting enamels and extensively published in the patent and journal literature.

There is however, no art which teaches compounds of Formula (1) in polyester compositions. Also, no prior art describing the use in coatings of compounds having the particular organic structure of both cycloaliphatic and linear aliphatic moieties in a single molecular entity as exhibited by the title compounds of this invention have been found.

COATINGS RESINS BASED ON 1,5-BIS-(4'-CARBOXYCYCLOHEXYL)-3-PENTANOLS AND CROSS-LINKING ENAMELS PREPARED THEREFROM

In specifying the number average molecular weight of a coatings resin, it is useful to refer to a "K" factor as the ratio of the total moles of polyester intermediates in the reaction mixture (Mt) to the total equivalents of carboxyl functionality (Ea) required for the reaction. The "K" factor is related to the polymer chain length by parameter "n". These relationships are shown mathematically in Equation 1.

$$K = \frac{M_t}{E_a} = \frac{1}{1 - 1/n} \qquad \text{Equation 1}$$

The value for the "n" parameter is estimated by dividing the desired polyester number average molecular weight by the average residual molecular weight of the reactants selected. The residual molecular weight is that portion of the reactant minus condensate, usually one mole of water or methanol. For the polyester coatings resins described in the examples which follow, a molecular weight of 2500 was selected. The preferred number average molecular weight range for the curable polyesters of the present invention is about 500 to 5000, with 2000 to 3000 being most preferred. Since the final coating molecular weight is to be considerably higher as a result of cross-linking reactions occurring during coating application, molecular weights for the polymer that are lower (or higher) would also be useful in describing this invention.

The ability to formulate a polyester coatings resin to a required number average molecular weight is highly desirable. This is accomplished by using "n" to calculate a starting point "K" factor which, in combination with other target values selected by the coatings chemist will define a unique polyester. Examples of other target value parameters are excess hydroxyl content, hydroxyl equivalent weight, acid value, carboxyl equivalent weight, molar or weight ratios of reactants and the like.

HYDROXYL OR BASE EXCESS RESIN PARAMETERS

The coatings resins generated from, for example, 1,5-bis-(4,-carboxycyclohexyl)-3-pentanol are preferably formulated using the "K" factor in combination with an "R" factor. The "R" factor is defined as the ratio of the total combining equivalents of base (hydroxyl), $E_b$, to the total combining equivalents of acid (carboxyl), $E_a$, (Equation 2 below). These two factors were found most useful in formulating novel coatings resins where the mixed (contain both hydroxyl and carboxyl groups on the same monomer) polyfunctional reactants of this invention are polymerized.

$$R = \frac{E_b}{E_a} \qquad \text{Equation 2}$$

The term $E_b$ of this invention means the total number of equivalents of all (100 mole percent of base) of the hydroxyl, amino, or epoxy functionality. This total is obtained by multiplying the number of moles of each reactant in this grouping by its functionality, i.e., the total number of basic reactive groups per mole of reactant that are capable of reacting with an acid or ester group. Similarly, the term $E_a$ means the total number of equivalents of all (100 mole percent of acid) of the carboxylic acid, anhydride or ester functionality. This total is obtained by multiplying the number of mole of each reactant in this grouping by its functionality, i.e., the total number of acidic reactive groups per mole of reactant that are capable of reacting with a hydroxy, amino, or epoxy group.

RESIN AND COATINGS PREPARATION PROCEDURES

Condensation polymerization reactions can be carried out using well known procedures. The most preferred method is to melt all reactants in a suitably sized reactor, heat the reactants to initiate the reaction, and continue processing until the desired molecular weight is reached. Reaction is evidenced by the collection of water (direct condensation) or alcohol (ester interchange). This procedure is referred to as fusion processing and can be conducted at atmospheric pressure or under vacuum. No modifications in these standard procedures are required for processing 1,5-Bis-(4'-carboxycyclohexyl)-3-pentanol or its esters.

The resin so produced can be dissolved in a suitable solvent, usually xylene, and formulated into an industrial baking enamel. To the resin solution are added a cross-linking resin (for example, hexamethoxymethylmelamine), pigments (rutile titanium dioxide), silicone or fluorocarbon flow control additives, acid catalysts, dispersing aids, additional solvents and other materials commonly used by the coatings industry in the manufacture of paints. No modifications in paint formulation procedures are required when resins derived from 1,5-Bis-(4'-carboxycyclohexyl)-3-pentanol or its esters are used.

Upon applying the formulated coatings to a metal substrate such as zinc phosphate pretreated cold roll steel sheeting, the advantages of incorporating 1,5-Bis-(4'-carboxycyclohexyl)-3-pentanol and its esters into the coating system are realized. Compared to a control system representing the most common, state-of-the-art, industrial polyester baking enamel, the coatings provided by the present invention have significantly improved hardness/flexibility balances plus excellent durability.

Thus, as a further aspect of the present invention, there is provided a curable polyester comprising (1) about 1 mole percent to about 20 mole percent of a residue of the formula

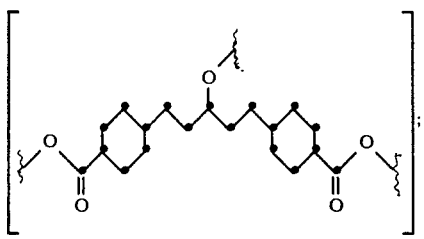

(2) diol and/or polyol residues; and
(3) dicarboxylic acid residues.

As a preferred embodiment of this aspect of the present invention, the polyester forming reaction mixture components are described by the following two limitations:

(a) the ratio of the total moles of polyester monomers in the polymerization reaction mixture to the total molar equivalents of carboxy/anhydride groups required for the reaction is about 1.01 to about 1.50; and (b) the total combining equivalents of hydroxyl groups to the total combining equivalents of carboxyl groups is from about 0.6 to about 1.4.

In such curable polyesters, suitable diol and/or polyol residues are preferably selected from ethylene glycol; propylene glycol; 1,3-propanediol; 2,4-dimethyl-2-ethylhexane-1,3-diol; 2,2-dimethyl-1,3-propanediol; 2-ethyl-2-butyl-1,3-propanediol; 2-ethyl-2-isobutyl-1,3-propanediol; 1,3-butanediol; 1,4-butanediol; 1,5-pentanediol; 1,6-hexanediol; 2,2,4-trimethyl-1,6-hexanediol; thiodiethanol; 1,2-cyclohexanedimethanol; 1,3-cyclohexanedimethanol; 1,4-cyclohexanedimethanol; 2,2,4,4-tetramethyl-1,3-cyclobutanediol; p-xylylenediol; diethylene glycol; triethylene glycol; tetraethylene glycol; and pentaethylene, hexaethylene, heptaethylene, octaethylene, nonaethylene, and decaethylene glycols.

Further, preferably the carboxylic acid residues are selected from oxalic; malonic, dimethylmalonic; succinic; glutaric; adipic; trimethyladipic; pimelic, 2,2-dimethylglutaric; azelaic; sebacic; fumaric; maleic; itaconic; 1,3-cyclopentanedicarboxylic; 1,2-cyclohexanedicarboxylic; 1,3-cyclohexanedicarboxylic; 1,4-cyclohexanedicarboxylic; phthalic; terephthalic; isophthalic; 2,5-norbornanedicarboxylic; 1,4-naphthalic; diphenic; 4,4,-oxydibenzoic; diglycolic; thiodipropionic; 4,4'-sulfonyldibenzoic; and 2,6-naphthalenedicarboxylic acids.

As a further aspect of the present invention, there is provided a cross-linkable enamel composition comprising a curable polyester comprising (1) about 1 mole percent to about 20 mole percent of a residue of the formula

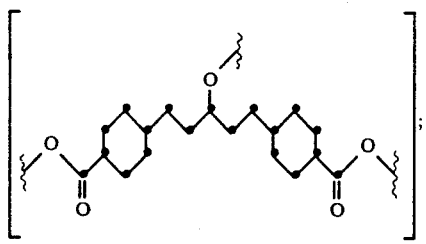

(2) diol and/or polyol residues;
(3) dicarboxylic acid residues; and
(4) a cross-linking agent.

As a preferred embodiment of this aspect of the present invention, the polyester forming reaction mixture components are described by the following two limitations:

(a) the ratio of the total moles of polyester monomers in the polymerization reaction mixture to the total molar equivalents of carboxy/anhydride groups required for the reaction is about 1.01 to about 1.50; and (b) the total combining equivalents of hydroxyl groups to the total combining equivalents of carboxyl groups is from about 0.6 to about 1.4.

In the above curable polyester composition, suitable cross-linking agents are preferably chosen from the types used in melamine-formaldehyde resins, benzoguanamine-formaldehyde resins, glycoluril-formaldehyde resins, epoxy resins, polymeric isocyanate resins, blocked isocyanate resins, and silicone resins. Most preferably, the cross-linking agent is selected from hexamethoxymethylamine, tetramethoxymethylbenzoguanamine, tetramethoxymethylurea, tetramethoxymethylglycoluril, poly(bisphenol A glycidyl ether), trimethylolpropane tris-toluenediisocyanate adduct, methyl iso-butyloxime blocked isophoronediisocyanate, and poly(phenylmethoxysilanes).

As a further aspect of the present invention there is provided a cross-linkable enamel composition as described above, further comprising one or more leveling and flow control agents; pigment wetting and dispersing agents; cross-linking catalysts; tinting pigments; defoaming and antifoaming agents; anti-settling, antisag, and bodying agents; anti-skinning agents; antiflooding and anti-floating agents; fungicides and mildewicides; thickening agents; or coalescing agents.

Such paint or coating additives as described above form a relatively minor proportion of the enamel composition, preferably about 0.05 weight % to about 5.00 weight %.

As a further aspect of the present invention, there is provided a curable enamel composition optionally containing one or more of the above-described additives, further comprising one or more pigments.

Pigments suitable for use in the enamel compositions envisioned by the present invention are the typical organic and inorganic pigments, well-known to one of ordinary skill in the art of surface coatings, especially those set forth by the Colour Index, 3rd Ed., 2d Rev., 1982, published by the Society of Dyers and Colourists in association with the American Association of Textile Chemists and Colorists. Examples include, but are not limited to the following: CI Pigment White 6 (titanium dioxide); CI Pigment Red 101 (red iron oxide); CI Pigment Yellow 42, CI Pigment Blue 15, 15:1, 15:2, 15:3, 15:4 (copper phthalocyanines); CI Pigment Red 49:1; and CI Pigment Red 57:1.

EXPERIMENTAL SECTION

The coatings test procedures followed in presenting the examples and results of this invention are standard to the industry and are as follows:
1. Acid Value of resins (ASTM Method D 465)
2. Testing Coated Metal Specimens at 100 Percent Relative Humidity - Cleveland humidity (ASTM Method D 2247)
3. Ford Cup Viscosity (ASTM Method D 1200)
4. Molecular Weight (Gel Permeation Chromatography)
5. Film Thickness (General Electric Gage, Type B)
6. Film Hardness (Pencil Method)
7. Solvent resistance (Methylethyl ketone (MEK) dynamic rub test (see ASTM Method D 1308)
8. Staining Tests (ASTM Method D 1540)
9. Specular Gloss (ASTM Method D 523)
10. Hegman Fineness-of-Dispersion (ASTM Method D 1210)

SECTION A

Synthesis of the Polymer Intermediates
1,5-Bis-(4'-Carboxycyclohexyl)-3-Pentanol and Its Methyl Ester

Part 1

Condensation of Methyl 4-Formyl Benzoate With Acetone

This procedure describes a typical base catalyzed condensation of methyl 4-formyl benzoate with acetone and is the procedure generally used.

A solution of 0.55 moles (90.3 g) of methyl 4-formyl benzoate was prepared under an inert atmosphere in a 1 L 3-necked flask using a mechanical stirrer. (The inert atmosphere is maintained throughout the reaction to minimize oxidation of the methyl 4-formyl benzoate.) To this solution was added 0.25 (14.5 g, 18.3 mL) moles of acetone. A cooling bath, consisting simply of an evaporating dish filled with cold tap water, was placed under the reaction vessel and a solution of 2.5 g (0.0625 moles) of NaOH in 25 mL of 1/1 methanol/water was added slowly using an addition funnel. The rate of addition is determined by the temperature of the reaction which is maintained at less than 35° C. The initial rate is deceptive as the reaction fails to begin with the initial addition, presumably due to the presence of acidic impurities in the starting materials.

When the reaction begins, the solution initially turns yellow and then a light yellow precipitate forms which eventually becomes a thick slurry. After 2.5 hrs. the reaction mixture is filtered and washed with methanol until the wash solution is no longer dark. The product was allowed to air dry on the filter to yield 82.9 g (95% yield) of 1,5-bis-(carbomethoxyphenyl)-1,4-pentadien-3-one. The product may be readily recrystallized from acetic acid or xylene. $^1$H NMR (CDCl$_3$) 270 MHz $\delta$=3.93 (s,6H), 7.15(d,2H, J=16 Hz), 7.68 (d,4H, J=10 Hz), 7.76 (d,2H, J=16 Hz), 8.09 (d,4H, J=10Hz). IR (KBr): 1720, 1653, 1284 cm$^{-1}$. Elemental Analysis: Calc. for C$_{21}$H$_{12}$O$_5$ : C,71.98; H,5.18. Found: C,71.98; H,5.15. m.p. 221°-223° C.

Part 2

Synthesis of 1,5-Bis-(4'-Carbomethoxycyclohexyl)-3-Pentanol Via Direct Hydrogenation of 1,5-Bis.(carbomethoxyphenyl)1,4-Pentadien-3-One (Route 1)

The following two examples demonstrate the preferred operation of the single step procedure (Route 1). In both cases the recovery is generally greater than 95%.

EXAMPLE 1 - Hydrogenation with 5% Rh on Carbon

A mixture of 1.0 grams of 5% Rh on carbon catalyst, 10.0 grams of 1,5-bis-(4'-carbomethoxyphenyl)-1,4-pentadien-3-one (2), and 100 mL of cyclohexane was prepared in a stainless steel autoclave. The autoclave was pressurized to 500 psi with hydrogen and then heated to 225° C. Upon reaching temperature, the pressure was adjusted to 1500 psi and these conditions were maintained for 5 hrs. The reaction was then cooled and vented. The product is soluble in the cyclohexane and is separated from the catalyst by filtration. The product is isolated by simple solvent removal in vacuo. The product was analyzed by GC. Characterization of the impurities and verification of the structure assignment of the products was accomplished via GC-MS. The identity of the desired 1,5-bis-(4'-carbomethoxycyclohexyl)-3-pentanol was further verified by comparison of retention times with very pure material attained by Route 2 (see Part 3 below).

GC Analysis (Area %)

1.5-bis-(4'-carbomethoxycyclohexyl)-3-pentanol: 87%
1,5-bis-(4'-carbomethoxycyclohexyl)-3-pentanone: 4%
1,5-bis-(4'-carbomethoxycyclohexyl)-pentane: 8%
1-(4'-carbomethoxycyclohexyl)-5-(4''-methylcyclohexyl)-3-pentanol: 1%

EXAMPLE 2 - Hydrogenation with 5% Pt on Carbon

The procedure described in Example 1 of this section was repeated with the exception that 5% Pt on carbon was used as a catalyst rather than Rh on carbon.

GC Analysis (Area %)

1.5-bis (4'-carbomethoxycyclohexyl)-3-pentanol: 88%
1,5-bis-(4'-carbomethoxycyclohexyl)-3-pentanone: 8%
1,5-bis-(4'-carbomethoxycyclohexyl)-pentane: 4%
1-(4'-carbomethoxycyclohexyl)-5-(4'''-methylcyclohexyl) 3-pentanol: 1%

EXAMPLES 3-6

These examples will demonstrate that other catalysts will generate the desired alcohol diester but are not as efficient, giving higher levels of impurity.

EXAMPLE 3 - Hydrogenation with 1% Pt on Silica

The procedure described in Example 1 of this section was repeated with the exception that 1% Pd on silica was used as a catalyst rather than Rh on carbon.

GC Analysis (Area %)

1.5-bis-(4'carbomethoxycyclohexyl)-3-pentanol: 75%
1,5-bis-(4'-carbomethoxycyclohexyl)-3-pentanone: 17%
1,5-bis-(4'-carbomethoxycyclohexyl)-pentane: 5%
1-(4'-carbomethoxycyclohexyl) 5-(4''-methylcyclohexyl)-3-pentanol: <1%

The mixture also contained 3% unhydrogenated aromatics.

EXAMPLE 4 - Hydrogenation with 1% Pt on Titania

The procedure described in Example 1 of this section was repeated with the exception that 1% Pt on titania was used as a catalyst rather than Rh on carbon.

GC Analysis (Area %)

1.5-bis-(4'carbomethoxycyclohexyl)-3-pentanol: 70%
1,5-bis-(4'carbomethoxycyclohexyl)-3-pentanone: 14%
1,5-bis-(4'-carbomethoxycyclohexyl)-pentane: <1%
1-(4 'carbomethoxycyclohexyl)-5-(4'-methylcyclohexyl)-3-pentanol: <1%

The mixture also contained 15% unhydrogenated aromatics.

EXAMPLE 5 - Hydrogenation with 0.5% Pd on Alumina

The procedure described in Example 1 of this section was repeated with the exception that 0.5% Pd on alumina was used as a catalyst rather than Rh on carbon.

GC Analysis (Area %)

1.5-bis-(4'-carbomethoxycyclohexyl)-3-pentanol: 63%
1,5-bis-(4'-carbomethoxycyclohexyl)-3-pentanone: 32%
1,5-bis-(4'-carbomethoxycyclohexyl)-pentane: <1%
1-(4'-carbomethoxycyclohexyl)-5-(4''-methylcyclohexyl)-3-pentanol: <1%

The mixture also contains 5% unhydrogenated aromatics.

EXAMPLE 6 - Hydrogenation with 1% Ru on Titania

The procedure described in Example 1 of this section was repeated with the exception that 1% Ru on titania was used as a catalyst rather than Rh on carbon.

GC Analysis (Area %)

1.5-bis-(4'-carbomethoxycyclohexyl)-3-pentanol: 60%
1,5-bis-(4'-carbomethoxycyclohexyl)-3-pentanone: 12%
1,5-bis-(4'-carbomethoxycyclohexyl)-pentane: 10%
1-(4'-carbomethoxycyclohexyl)-5-(4''methylcyclohexyl)-3-pentanol: <1%

The mixture also contained 18% unhydrogenated aromatics.

PART 3

Synthesis of 1,5-Bis-(4'-Carbomethoxycyclohexyl)-3-Pentanol Via Sequential Hydrogenation of 1,5-Bis-(Carbomethoxyphenyl)1,4-Pentadien-3-One - (Route 2)

The following procedures are exemplary of the manner in which the two step process (Route 2) is performed.

Step 1

Hydrogenation of 1,5-bis-(4,-carbomethoxyphenyl)1,4-pentadien-3-one

A mixture of 175 g (0.50 moles) of 1,5-bis-(4,carbomethoxyphenyl)1,4-pentadien-3-one, 17.5 g copper-chromite, and 1750 mL of toluene were placed in a stainless steel autoclave. The autoclave was pressurized to 250 psi with hydrogen and then heated to 180° C. Upon reaching the desired temperature the pressure was adjusted to 1000 psig with hydrogen. The temperature and pressure were maintained at these levels for 5 h. The autoclave was then cooled and vented. The mixture was removed from the autoclave and transferred to a 2 L Erlenmeyer flask where the mixture was heated to >90° C. and then filtered through a steam jacketed Buchner funnel using a pad of Celite Filter-Aid to assist in catalyst removal. The solution was allowed to cool to room temperature and was filtered to give 142.1 g of 1,5-bis-(4'-carbomethoxyphenyl)-3-pentanol as a fluffy, white crystalline product. The volume of the mother liquor was reduced in vacuo to a level of 500-600 mL, heated to dissolve any solids, and crystallized to give an additional 13.9 g. Reducing the volume to 250 mL yielded an additional 5.2 g. All three batches of crystals were indistinguishable by chromatography and were combined to give a total of 161.2 g (0.453 moles, 91% yield) of 1,5-bis-(4'-carbomethoxyphenyl)-3-pentanol. 270 MHz $^1$H NMR (CDCl$_3$) $\delta=1.81$ (t,4H), 2.77 (m,4H), 3.61 (m,1H), 3.88 (s,6H), 7.21 (d,4H), 7.91 (d,4H). IR (KBr): 1720, 1290 cm$^{-1}$; (mull) 3460 cm$^{31}$ $^1$. FDMS (M+/e): 356. Elemental Analysis: Calc. for $C_{21}H_{24}O_5$: C,70.77; H,6.79. Found: C,71.09; H,6.68. m.p. 129°–130° C.

Step 2

Hydrogenation of 1,5-bis-(4'-carbomethoxyphenyl)-3-pentanol

To a stainless steel autoclave was added 143.9 g (0.404 moles) 1,5.bis-(4,-carbomethoxyphenyl)-3-pentanol, 14.4 grams of 0.5% Pd on alumina, and 1,150 mL of cyclohexane. The autoclave was pressurized to 500 psi with hydrogen and then heated to 225° C. Upon reaching temperature, the pressure was adjusted to 1500 psi and these conditions were maintained for 6 hrs. The reaction was then cooled and vented. The product is soluble in the cyclohexane and is separated from the catalyst by filtration. The product is isolated by simple solvent removal in vacuo to give 139.6 grams of product (0.379 moles, 94%) consisting of all three diastereomeric cyclohexyl isomers of 1,5-bis-(4'-carbomethoxycyclohexyl)-3-pentanol. 300 MHz NMR (CDCl$_3$) $\delta=0.93$ (m,2H), 1.10–1.65 (m, 20H), 1.82 (d,1H), 1.96 (d,4H), 2.23 (m,1H), 2.52 (m,1H), 3.53 (s(br),1H), 3.67 (s,3H), 3.69 (s,3H). IR (neat): 1040, 1200, 1740, 3500 cm$^{-1}$. GC.MS: (a) electron impact 50 eV: all three isomers with identical mass spectra: 368(<1%), 350, 337, 318, 290, 199, 170, 167, 138, 121, 108, 95, 94, 87, 81, 67. (NH$_3$ chemical ionization): three peaks with M+=368.

Part 4

Hydrolysis of 1,5-Bis-(4'-Carbomethoxycyclohexyl)-3-Pentanol to 1,5-Bis-(4'-Carboxycyclohexyl)-3-Pentanol To a 2 L round bottomed flask was added 352 g (0.957 moles) of 1,5-bis-(4'-carbomethoxycyclohexyl) 3-pentanol and a solution of 115 g (2.88 moles) of sodium hydroxide in 900 mL of water. The flask was then equipped with a Vigreaux column and a distillation head and heated to reflux. Methanol was removed periodically by taking distillation fractions at intervals. This was accomplished by removing any distillate boiling at less than 90° C. All the methanol was apparently removed in 8–9 hrs and the reaction was allowed to continue for a total of 10 hrs. A small amount of material was insoluble in the aqueous layer and was removed by decantation. The aqueous solution was then acidified by adding the basic solution to a mixture of 275 mL concentrated hydrochloric acid and 600 g of ice. The resultant slurry was transferred to a large separatory funnel and extracted three times with 1 L of ethyl acetate. The ethyl acetate layers were dried over anhydrous sodium sulfate and then most of the solvent was removed in vacuo. Most of the remaining ethyl acetate was removed on a vacuum pump, first at room temperature, and then at 60° C. The material foams severely, limiting the level of solvent removal. The product weighed 316.78 g and assayed as still containing 14% ethyl acetate by weight. (Yield: 97% accounting for retained ethyl acetate.) The product is a glass-like material at room temperature which upon heating to 50°–60° C. forms a thick, transferable syrup. 300 MHz NMR (CDCl$_3$) $\delta=0.80$–1.05 (m,2H), 1.05–1.65 (m, 20H), 1.83 (d,1H), 2.01 (d, 4H), 2.25 (m,1H), 2.68 (m,1H), 3.56 (s(br),1H). FDMS (M+/e): 340.

SECTION B

Calculation, Synthesis and Evaluation of Polyester Coatings Resins Generated from 1,5-Bis-(4-Carboxycyclohexyl)-3-Pentanol and its Esters

EXAMPLE 1

By way of an example for estimating chain length, "n", the "K" factor and the "R" factor, consider a target resin molecular weight of 2500 and a desired hydroxyl excess of 20 equivalent percent:

| Reactant | Molecular Weight Actual | Residual |
| --- | --- | --- |
| NPG Glycol[a] | 104 | 86 |
| Isophthalic Acid | 166 | 148 |
| Adipic Acid | 146 | 128 |
| BCPP[b] | 340 | 322 |
| Average | — | 171 |

[a]2,2-dimethyl-1,3-propanediol
[b]1,5-Bis-(4'-Carboxycyclohexyl)-3-Pentanol

The residual molecular weight is that portion of the reactant remaining and incorporated in the product after condensation polymerization. In this example, the average chain length ,"n", is 2500/171 or 15. Substituting into Equation 1, one obtains a "K" value of 1.07 which can be used with the required "R" value of 1.20 to generate a set of simultaneous equations to calculate the required number of moles of each reactant. Examples 2–4 show the final compositions of coatings resins arrived at through this procedure.

EXAMPLE 2 - Coatings Resin Prepared From 1,5-Bis-(4'-Carboxycyclohexyl)-3-Pentanol This polyester reactant contains both carboxyl hydroxyl functional groups. For the purpose of satisfying the relationship between the "K" and "R" values as defined above, the molar and equivalent amounts of these reactants are proportionally distributed based on the ratio of the two types of functional groups.

1,5-Bis-(4'-carboxycyclohexyl)-3-pentanol (Ia) along with 2,2-dimethyl-1,3-propanediol (NPG), isophthalic acid (IPA), and adipic acid (AD) were selected as raw materials to demonstrate the improvement in flexibility without loss of hardness. Using a "K" value of 1.07 and an "R" value of 1.2, equations 1 and 2 were solved simultaneously to give the reactor charge for Resin A (Table I). In the tabulation the charge and molar percents of the mixed reactant, Ia, is shown proportioned by its functionality type (hydroxyl:carboxyl) ratio of 1:2. For "K" and "R" value calculations, its functionality is taken as 3.

TABLE I

| Reactant | Moles | Resin A Mole % | Equivalents | Charge |
|---|---|---|---|---|
| Base Components | | | | |
| NPG | 1.877 | 95.81 | 3.753 | 195.8 |
| Ia | 0.082 | 4.19 | 0.246 | 27.9 |
| Acid Components | | | | |
| Ia | 0.165 | 10.46 | 0.495 | 56.1 |
| IPA | 0.706 | 44.77 | 1.412 | 117.0 |
| AD | 0.706 | 44.77 | 1.412 | 103.0 |

K Value = $M_t/E_a$ = 3.536/3.319 = 1.065
R Value = $E_b/E_a$ = 3.999/3.319 = 1.205

Polymerization was carried out in one stage. The total charge weights in grams of each reactant were placed in a one-liter, three-necked, reaction flask equipped with a stirrer, a steam-jacketed partial condenser and a glass fitting holding a nitrogen sparge tube and thermocouple wires. A catalytic amount of butyl stannoic acid (0.1 % based on reactor charge) was added and the contents heated to 170° C., 180° C. and 190° C. with the temperature held for two hours after each incremental increase. At a temperature of 190° C, the acid value (mg KOH per gram product) was monitored while condensate (water) was collected. The reaction was considered complete when an acid value of 5 mg KOH/g polymer was obtained. Cooling to 120° C. was followed by the slow addition of xylene to give a resin/solvent ratio of 85/15. The resin had a melt viscosity of 6.3 P at 100° C. as measured on an Atlas ICI cone and plate viscometer and a number average molecular weight of 2400 by gel permeation chromatography. The xylene solution had a Brookfield viscosity of 300 P at 25° C.

EXAMPLE 3 - Coatings Resin Prepared From 1,5-Bis-(4'-Carbomethoxycyclohexyl)-3-Pentanol 2,2-Dimethyl-1,3-propanediol (NPG), isophthalic acid (IPA), and adipic acid (AD) were selected to demonstrate that the methyl ester of compound Example 2 will also provide coatings with an improvement in flexibility without loss of hardness. Using a "K" value of 1.07 and an "R" value of 1.2, equations 1 and 2 were solved simultaneously to give the reactor charge for Resin B (Table II). In the tabulation the charge and molar percents of the mixed reactant, 1,5-bis-(4'-carbomethoxycyclohexyl)-3-pentanol, (IIa) is shown proportioned by its functionality type (hydroxyl:carboxyl) ratio of 1:2. For "K" and "R" value calculations, its functionality is taken as 3.

TABLE II

| Reactant | Moles | Resin B Mole % | Equivalents | Charge |
|---|---|---|---|---|
| Base Components | | | | |
| NPG | 1.843 | 95.79 | 3.690 | 193.0 |
| IIa | 0.081 | 4.21 | 0.243 | 30.0 |
| Acid Components | | | | |
| IIa | 0.163 | 10.56 | 0.489 | 60.0 |
| IPA | 0.690 | 44.72 | 1.380 | 115.0 |
| AD | 0.690 | 44.72 | 1.380 | 102.0 |

K Value = $M_t/E_a$ = 3.467/3.249 = 1.067
R Value = $E_b/E_a$ = 3.933/3.249 = 1.210

Resin B had a melt viscosity of 7.0 P at 100° C. as measured on an Atlas ICI cone and plate viscometer and a number average molecular weight of 1800 by gel permeation chromatography. An 85/15 resin/xylene solution had a Brookfield viscosity of 81 P at 25° C.

EXAMPLE 4

A control resin which is formulated with 1,1,1-trimethylolpropane (TMP) to induce branching and provide hydroxyl-group functionality for cross-linking reactions was prepared. As in Resins A and B this reference material was prepared with 2,2-dimethyl-1,3-propanediol (NPG), isophthalic acid (IPA) and adipic acid (AD); however, no 1,5-bis-(4,-Carboxycyclohexyl)-3-Pentanol or its esters were incorporated. Table III shows the composition of control Resin C.

TABLE III

| Reactant | Moles | Resin C Mole % | Equivalents | Charge |
|---|---|---|---|---|
| Base Components | | | | |
| NPG | 2.028 | 86.78 | 4.056 | 210.9 |
| TMP | 0.309 | 13.22 | 0.927 | 41.4 |
| Acid Components | | | | |
| IPA | 1.030 | 50.00 | 2.060 | 171.0 |
| AD | 1.030 | 50.00 | 2.060 | 150.4 |

K Value = $M_t/E_a$ = 4.397/4.120 = 1.067
R Value = $E_b/E_a$ = 4.983/4.120 = 1.210

Resin C had a melt viscosity of 8.0 P at 100° C. as measured on an Atlas ICI cone and plate viscometer and a number average molecular weight of 1800 by gel permeation chromatography. An 85/15 resin/xylene solution had a Brookfield viscosity of 125 P at 25° C.

EXAMPLE 5

A white baking enamel was prepared by blending the following in a suitable container and dispersing the titanium dioxide pigment with a high speed mixer such as a "Waring" blender or an IKA "Ultra-Turrax" homogenizer.

| Ingredient | Amount |
|---|---|
| Resin (85% Solids) | 150.0 grams |
| Solvent Blend[a] | 77.0 |
| DuPont R-900 TiO$_2$ | 121.4 |
| Cyanamid's "CYMEL 303" | 54.6 |
| p-Toluenesulfonic Acid | 0.8 |
| 3M Company's "FC-430" | 0.2 |

[a]70% Methyl Amyl Ketone, 15% Ethoxyethyl propionate, 15% n-butanol

Additional solvent blend was added to obtain a viscosity of 30 seconds using the Number 4 Ford Cup Viscometer. The enamel was judged acceptable for spraying onto zinc phosphate pre-treated test panels when a Hegman Grind Fineness value of 7-8 was obtained.

EXAMPLE 6

Test panels from enamels prepared from Resins A, B, and C as given in Example 5 were sprayed onto 20 gauge zinc phosphate pre-treated metal panels and baked in a forced air oven at 300° F. for 30 minutes to give cured film thickness of 0.8-1.2 mils. The test panels were subjected to a variety of performance evaluations as summarized in Table IV.

TABLE IV

Evaluation[1] of Enamels Prepared from Resins Based on 1,5-Bis-(4'-Carboxycyclohexyl)-3-Pentanol and Its Esters

| Resin | Pencil Hardness | Impact Strength | | Initial 60° Gloss | Cleveland Humidity | | MEK Rub Test | Stain Test Iodine | |
|---|---|---|---|---|---|---|---|---|---|
| | | Direct | Reverse | | Blisters | Gloss Retained | | 5' | 30' |
| A | 5H | 160 | 160 | 93.8 | none | 98.2 | 220 | 3 | 2 |
| B | 3H | 160 | 160 | 93.5 | none | 96.4 | 190 | 4 | 3 |
| C | 2H | 160 | 140 | 85.6 | none | 69.6 | 250 | 4 | 3 |

[1]Impact Strength values are inch pounds.
Cleveland Humidity test was 100 hours at 140° F.
MEK is Methyl Ethyl Ketone - Values are double rubs.

We claim:

1. A curable polyester comprising
   (1) about 1 mole percent to about 20 mole percent of a residue of the formula

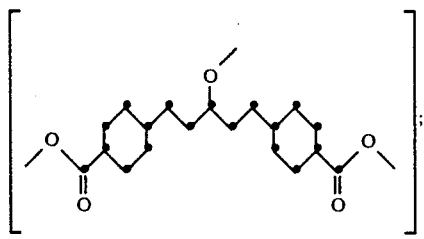

(2) diol and/or polyol residues; and
   (3) dicarboxylic acid residues.

2. The curable polyester of claim 1, wherein in the reaction mixture which yields said curable polyester,
   (a) the ratio of the total moles of polyester monomers in the polymerization reaction mixture to the total molar equivalents of carboxy/anhydride groups required for the condensation reaction is about 1.01 to about 1.50; and
   (b) the total combining equivalents of hydroxyl groups to the total combining equivalents of carboxyl groups is from about 0.6 to about 1.4.

3. The curable polyester of claim 1, wherein the dicarboxylic acid residue(s) is (are) selected from residues of oxalic; malonic, dimethylmalonic; succinic; glutaric; adipic; trimethyladipic; pimelic, 2,2.dimethylglutaric; azelaic; sebacic; fumaric; maleic; itaconic; 1,3-cyclopentanedicarboxylic; 1,2-cyclohexanedicarboxylic; 1,3-cyclohexanedicarboxylic; 1,4-cyclohexanedicarboxylic; phthalic; terephthalic; isophthalic; 2,5-norbornanedicarboxylic; 1,4-naphthalic; diphenic; 4,4'-oxydibenzoic; diglycolic; thiodipropionic; 4,4'sulfonyldibenzoic; and 2,5-naphthalenedicarboxylic acids;
   and the diol and/or polyol residue(s) is (are) selected from residues of ethylene glycol; propylene glycol; 1,3-propanediol; 2,4-dimethyl-2-ethylhexane-1,3-diol; 2,2-dimethyl-1,3-propanediol; 2-ethyl-2-butyl-1,3-propanediol; 2-ethyl-2-isobutyl-1,3-propanediol; 1,3-butanediol; 1,4-butanediol; 1,5-pentanediol; 1,6-hexanediol; 2,2,4-trimethyl-1,6hexanediol; thiodiethanol; 1,2-cyclohexanedimethanol; 1,3-cyclohexanedimethanol; 1,4-cyclohexanedimethanol; 2,2,4,4-tetramethyl-1,3-cyclobutanediol; p-xylylenediol; diethylene glycol; triethylene glycol; tetraethylene glycol; and pentaethylene, hexaethylene, heptaethylene, octaethylene, nonaethylene, and decaethylene glycols.

4. A coating obtained upon the polymerization of the curable polyester composition of claim 1.

5. A casted or molded article obtained upon the polymerization of the curable polyester of claim 1.

* * * * *